(12) United States Patent
Lai et al.

(10) Patent No.: US 7,745,647 B2
(45) Date of Patent: Jun. 29, 2010

(54) **DITERPENES FROM THE FRUITING BODY OF *ANTRODIA CAMPHORATA* AND PHARMACEUTICAL COMPOSITIONS THEREOF**

(75) Inventors: Min-Nan Lai, Nantou County (TW); Yueh-Hsiung Kuo, Taipei (TW); Young-Ji Shiao, Taoyuan (TW)

(73) Assignee: Kang Jian Biotech Corp, Ltd., Nantou County ( * ) Notice: Subject to any disclaimer, the term of this patent is extended or adjusted under 35 U.S.C. 154(b) by 0 days.

(21) Appl. No.: 12/318,294

(22) Filed: Dec. 24, 2008

(65) Prior Publication Data
US 2009/0118364 A1    May 7, 2009

Related U.S. Application Data

(63) Continuation of application No. 11/586,001, filed on Oct. 25, 2006, now Pat. No. 7,601,854.

(51) Int. Cl.
C07D 305/12 (2006.01)
A01N 43/08 (2006.01)
(52) U.S. Cl. ........................ 549/323; 514/473
(58) Field of Classification Search ................ 549/323; 514/472
See application file for complete search history.

(56) References Cited

U.S. PATENT DOCUMENTS 7,601,854 B2 * 10/2009 Lai et al. .................. 549/323

OTHER PUBLICATIONS

Chen et al. Journal of Natural Products (2006), 69(4), 689-691.*
CC Chen, et al. "Neuroprotective diterpenes from the fruiting body of *Antrodia camphorata*", J. Nat Prod, Apr. 2006, vol. 69, No. 4, Abstract, http://www.ncbi.nlm.nih.gov.
Clardy, John, Using genomics to deliver natural products from symbiotic bacteria, Genome Biology, 2005, 6:232.
Pal et al., Chemical Transformation of Andrographolide, Indian Journal of Chemistry, Section B: Organic Chemistry Including Medicinal Chemistry, 2002, 41B(9), 1915-1918 Abstract.
* cited by examiner

*Primary Examiner*—Janet L Andres
*Assistant Examiner*—Nizal S Chandrakumar
(74) *Attorney, Agent, or Firm*—Bacon & Thomas, PLLC

(57) ABSTRACT

The present invention relates to novel diterpene compounds isolated from the fruiting body of *Antrodia camphorata*, especially to the new compounds of following structural formula:

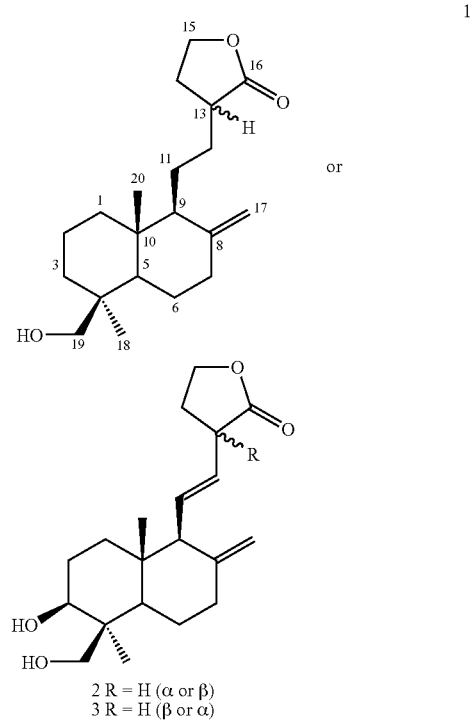

2 R = H (α or β)
3 R = H (β or α)

and pharmaceutically acceptable salt, solvate, hydrate or biologically active equivalent thereof. The present invention also relates to a pharmaceutical composition containing at least one of the novel diterpene compounds, and a use of the diterpene compound as a neuroprotective agent.

6 Claims, 1 Drawing Sheet

Key NOESY correlation for compound 1

DITERPENES FROM THE FRUITING BODY OF *ANTRODIA CAMPHORATA* AND PHARMACEUTICAL COMPOSITIONS THEREOF

CROSS-REFERENCE TO RELATED APPLICATION

This application is a Continuation of application Ser. No. 11/586,001 filed on Oct. 25, 2006.

FIELD OF THE INVENTION

The present invention relates to novel diterpene compounds isolated from the fruiting body of *Antrodia camphorata*. The in vitro neuroprotective activity of the new compounds was evaluated to demonstrate their utility as a pharmaceutical agent.

BACKGROUND OF THE INVENTION

*Antrodia camphorata* Wu, Ryvarden & Chang (classified into Polyporaceae, Aphyllophorales) is a parasitic fungus on the endemic species *Cinnamomum kanehirai* Hay (Lauraceae), which is an endangered species in Taiwan. Because of its endemic unique and rare utility in pharmacology, *A. camphorata* possesses high values in commercial and research area, and therefore it is the rarest and most expensive wild fungus in Taiwan nowadays.

*A. camphorata* only grows on the inner heartwood wall of the stem of *Cinnamomum kanehirai* Hay (Lauraceae) of more than one hundred years old, or on the moist wood surface of dead cowcamphor trees in Taiwan mountain area of 450-2000 m above sea level. *A. camphorata* gows in a dark, moist and low-temperatured environment with a very slow growth rate. Thus, it takes a quite long time to produce fruiting body in the nature. Wild *A. camphorata* grows on old cowcamphor trees, producing its fruiting body from the inner wall of the hollow tree stem. The fruiting body of *A. camphorata* exhibits various morhphology, with shapes of sheet, bell, horseshoe, or tower. The color of new-born fruiting body is florid, then turns to white, pale sorrel, hazel, or tan at growing.

Traditionally, this fungus has been used as a Chinese remedy for food and drug intoxication, diarrhea, abdominal pain, hypertension, itching of the skin, and liver cancer (see, for example, Tsai, Z. T.; Liaw, S. L. *The Use and the Effect of Ganoderma*; Sang-Yun Press: Taichung, Taiwan, 1982; p 116). In current biological studies, the fruiting bodies exhibited immunomodulating, antioxidative, and hepatoprotective effects (Hsiao, G. et al., J. R. *J. Agric. Food Chem.* 2003, 51, 3302-3308). The cultured mycelia have shown to have anti-inflammatory activity, vasorelaxation, cytotoxic activity against several tumor cell lines, protective activity of oxidative damage in normal human erythrocytes, and anti-hepatitis B virus activity (see, for example, Liu, J. J. et al., *Toxicol. Appl. Pharmacol.* 2004, 201, 186-193; Hseu,Y. C. et al., *Life Sci.* 2002, 71, 469-482; and Lee, I. H. et al., *FEMS Microbiol Lett.* 2002, 209, 63-67).

There are many biologically active materials contained in *A. camphorata*, such as polysaccharides, triterpenoids, SOD (peroxidase), adenosine, small molecular proteins, vitamins, trace elements, nucleic acids, steroids, pressure stablizing agents and so on. The only chemical study of the cultured mycelia of *A. camphorata* was conducted by Nakamura et al., found five cytotoxic maleic and succinic acid derivates (Nakamura, N. et al., *J. Nat. Prod.* 2004, 67, 46-48). Previous chemical studies of the fruiting body of *A. camphorata* have led to reports of several components including fatty acids, lignans, phenyl derivatives, sesquiterpenes, steroids, and triterpenoids (see, for example, Chen, C. H.; Yang, S. W. *J. Nat. Prod.* 1995, 58, 1655-1661; Cherng, I. H.; Wu, D. P.; Chiang, H. C. *Phytochemistry* 1996, 41, 263-267; and Shen, C. C. et al., *J. Chin. Med.* 2003, 14, 247-258).

In the present invention, we report the isolation and structural elucidation of three new labdane diterpenoids (1-3) from the fruiting body of *A. camphorata*, that is 19-hydroxylabda-8(17)-en-16,15-olide (1), 3,β,19-dihydroxylabda-8(17),11E-dien-16,15-olide (2), and 13-epi-3β,19-dihydroxylabda-8(17),11E-dien-16,15-olide (3), together with four known compounds, 19-hydroxylabda-8(17),13-dien-16,15-olide (4), 14-deoxy-11,12-didehydroandrographolide (5), 14-deoxyandrographolide, and pinusolidic acid. The three novel compounds and four compounds of known structure were evaluated for their neuroprotective effects in an in vitro test system.

SUMMARY OF THE INVENTION

In a first aspect, the present invention provides novel diterpene compounds isolated from the fruiting body of *Antrodia camphorate*.

The present invention provides a novel compound of following formula 1:

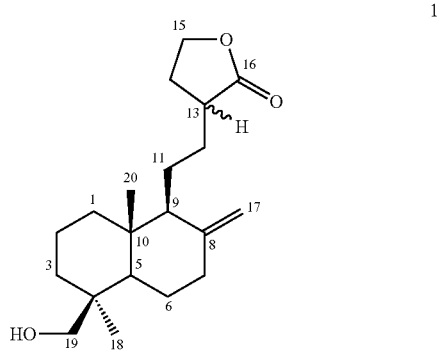

and a pharmaceutically acceptable salt, solvate, hydrate or biologically active equivalent or derivative thereof.

The present invention also provides a novel compound of following formula 2 or 3:

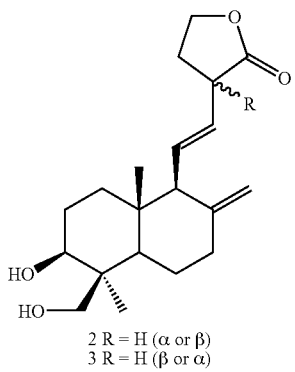

2 R = H (α or β)
3 R = H (β or α)

wherein R is H, and a pharmaceutically acceptable salt, solvate, hydrate or biologically active equivalent or derivative thereof.

In a second aspect, the present invention provides a pharmaceutical composition comprising at least one of the novel diterpene compounds disclosed in the invention, or a pharmaceutically acceptable salt, solvate, hydrate or biologically active equivalent or derivative thereof. In one embodiment of the invention, the present invention provides a pharmaceutical composition for the treatment, prophylaxis, and amelioration of neuron damages caused by drugs or aging, such as Alzheimer disease (AD, also known as a neurodegenerative disorder). In another embodiment, a composition of the invention comprises one or more prophylactic or therapeutic agents other than a compound of the invention, or a pharmaceutically acceptable salt, solvate, hydrate or biologically active equivalent or derivative thereof. In still another embodiment of the invention, the present composition comprises one or more the novel diterpene compounds disclosed in the invention, or a pharmaceutically acceptable salt, solvate, hydrate or biologically active equivalent or derivative thereof, combined with a pharmaceutically acceptable carrire, dilutant or excipient.

In a preferred embodiment, a composition of the invention is a pharmaceutical composition or as a single unit dosage form. Pharmaceutical compositions and dosage forms of the invention comprise one or more active ingredients in relative amounts and formulated in such a way that a given pharmaceutical composition or dosage form can be used to treat or prevent proliferative disease, such as cancer. The preferable pharmaceutical composition and dosage form contain a compound of formula 1, 2, 3, 4 or 5, 14-deoxyandrographolide, or pinusolidic acid, or a pharmaceutically acceptable salt, solvate, hydrate or biologically active equivalent or derivative thereof, optionally combined with one or more additional active agents.

Other properties of the invention will be obvious after the detailed disclosure of following examples and appending drawing.

DETAILED DESCRIPTION OF THE INVENTION

Figure 1:
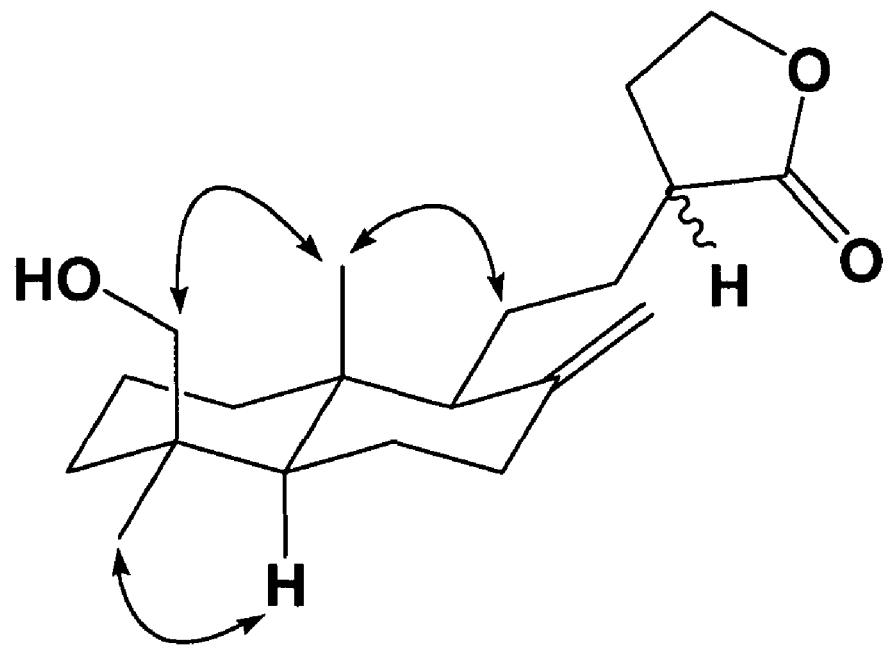
FIG. 1 shows the Key NOESY correlation for 1.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

In the following examples, specific rotations were recorded on a JASCO DIP-1000 digital polarimeter. IR spectra were recorded on a Perkin-Elmer 983 G spectrometer. $^1H$ and $^{13}C$ NMR spectra were recorded on a Varian Unity Plus-400 spectrometer. EIMS and HREIMS were measured with a JEOL Finnigan TSQ-46C and JEOL SX-102A mass spectrometers. Extracts were chromatographed on silica gel (Merck 70-230 mesh, 230-400 mesh) and purified on a semi-preparative normal-phase HPLC column [250×10 mm, Licrosorb Si 60 (7 μm)] carried out with a LCD Refracto Monitor III. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Example 1

Isolation and Characterization of Compound 1-3

The fruiting bodies of *A. camphorata* (No. 2) were provided by Kang Jian Biotech Corp. Ltd., Nantau, Taiwan, Republic of China. The fungus was identified by Dr. Tun-Tschu Chang of the Division of Forest Protection, Taiwan Forest Research Institute. A voucher specimen (No. 35396) was deposited in the herbarium of Taiwan Forestry Research Institute, Taipei, Taiwan.

The dried fruiting bodies of *A. camphorata* (2 kg) were extracted with MeOH (40 L) at room temperature (5 days twice). After evaporation, the residue of the MeOH extract was mixed with $H_2O$ to bring the total volume to 1 L. This phase was extracted with 1 L of EtOAc (3 times), the combined organic phase was evaporated, and the obtained black syrup (150 g) was chromatographed on silica gel eluting with hexane and EtOAc solutions. The fraction eluted with 30-40% EtOAc in hexane was separated and purified by HPLC using a preparative silica gel column and a mixture of EtOAc/hexane (3:7) as eluent to give The EtOAc-soluble fraction, which was chromatographed repeatedly to afford three pure new compounds, compound 1 (8.2 mg, $t_R$: 5'25"), compound 2 (19.4 mg, $t_R$: 8'40"), and compound 3 (3.0 mg, $t_R$: 8'45"); along with four known labdane diterpenoids, 19-hydroxylabda-8(17),13-dien-16,15-olide (compound 4, 32.4 mg, $t_R$: 5'50"), 14-deoxy-11,12-didehydroandrographolide (compound 5, 5.5 mg, $t_R$: 9'55"), 14-deoxyandrographolide (6.2 mg, $t_R$: 9'10"), and pinusolidic acid (3.1 mg, $t_R$: 11'25"). The structures of the known compounds were established by comparison of their spectroscopic data with literature values.

Compound 1 was isolated as an amorphous powder, and its molecular formula of $C_{20}H_{32}O_3$ was established through analysis of its $^{13}C$ NMR (shown in Table 1) and HREIMS data. The IR spectrum of 1 confirmed the presence of a γ-lactone group (1772 $cm^{-1}$) and a hydroxyl group (3470 $cm^{-1}$). The $^1H$ NMR spectrum (shown in Table 1) exhibited signals for two primary methyl groups [$δ_H$ 0.62 and 0.95 (3H each, s)], two methylene protons linked to a γ-lactone group [$δ_H$ 4.16 (td, J=8.8, 6.8 Hz) and 4.30 (td, J=8.8, 2.8 Hz)], a pair of olefinic protons [$δ_H$ 4.50 and 4.80 (1H each, br s)], two germinal carbinol protons [$δ_H$ 3.36 and 3.72 (1H each, d, J=11.2 Hz)]. The $^1H$ NMR data were almost same as those of known compound 4 except for that of $H_2$-15 and one more olefinic proton for compound 4 (see, Han, B. H. et al., *J. Med. Chem.* 1998, 41, 2626-2630). The consecutive protons from $δ_H$ 1.0 to 2.0 were revealed from the COSY and the HMBC spectra and clarified their relative locations. The $^{13}C$ NMR data (shown in Table 1) and DEPT spectroscopic analysis showed 20 signals including two $CH_3$, eleven $CH_2$, three CH, three C and one lactone carbonyl carbon. The lactone carbonyl carbon was assigned to C-16 on the basis of the HMBC spectrum. The two methylene protons linked to the γ-lactone group were correlated to C-13 at $δ_C$ 39.5, C-14 at $δ_C$ 29.6, and C-16 at $δ_C$ 179.1. In the same experiment, interactions were evidenced between the $H_2$-19 methylene protons at $δ_C$ 3.36 and 3.72 with the carbons C-3 at δ 35.4, C-4 at δ 39.6, C-5 at δ 57.1, and C-18 at δ 27.1. The NOESY spectrum (shown in FIG. 1) confirmed that the C-20 methyl group, $H_2$-11, and $H_2$-19 are on the same side of the molecule. The C-13 stereochemistry is uncertain. Based on the above evidence, the structure of compound 1 was proposed as 19-hydroxylabda-8(17)-en-16,15-olide.

Compound 2 was isolated as an amorphous powder. The molecular formula of $C_{20}H_{30}O_4$ was determined on the basis of HREIMS and $^{13}C$ NMR data (shown in Table 1). The IR absorption bands at 3381 cm$^{-1}$ and 1777 cm$^{-1}$ indicated the presence of hydroxyl and γ-lactone functionalities. The $^1$H NMR spectrum (shown in Table 1) exhibited signals for two primary methyl groups [δ$_H$ 0.72 and 1.22 (3H each, s)], and two methylene protons linked to a r-lactone group [δ$_H$ 4.23 (td, J=8.4, 6.8 Hz), δ$_H$ 4.34 (td, J=8.4, 3.6 Hz)], a pair of terminal methylene protons [δ$_H$ 4.50 and 4.74 (1H each, d, J=1.6 Hz)], a pair of trans-coupling olefinic protons [δ$_H$ 5.50 (dd, J=15.6, 5.6 Hz) and 5.64 (dd, J=15.6, 9.6 Hz)], a carbinol 1775 cm$^{-1}$ confirmed the presence of hydroxyl groups and a γ-lactone group. As a result of the assignment of the HMBC and HMQC spectra, the gross structure of compound 3 was shown to be the same as that of compound 2. From the analysis of NOESY spectrum, the relative configuration of the molecule and the side chain at C-9 was assigned as the same as compound 2. Analysis of all the data obtained suggested that compound 3 is the 13-epimer of 2 and proposed as 13-epi-3β,19-dihydroxylabda-8(17), 11E-dien-16,15-olide.

TABLE 1

NMR Data (CDCl$_3$, 400 MHz) for Compounds 1-3 [δ in ppm, mult. (J in Hz)]

| position | 1 δ$_C^a$ | 1 δ$_H$ | 2 δ$_C^a$ | 2 δ$_H$ | 3 δ$_C^a$ | 3 δ$_H$ |
|---|---|---|---|---|---|---|
| 1 | 39.0 t | 1.05 td (13.2, 5.2) 1.58 m | 38.2 t | 1.10 td (14.0, 4.4) 1.45 dt (14.0, 3.6) | 38.3 t | 1.12 td (13.2, 4.8) 1.60 dt (13.2, 4.0) |
| 2 | 19.0 t | 1.56 m 1.82 m | 23.0 t | 1.75 m | 23.3 t | 1.80 m 1.29 m |
| 3 | 35.4 t | 1.31 m 1.89 m | 80.7 d | 3.45 dd (11.2, 4.4) | 80.8 d | 3.46 dd (11.2, 5.2) |
| 4 | 39.6 s | | 42.9 s | | 43.2 s | |
| 5 | 57.1 d | 1.22 dd (12.8, 2.4) | 54.6 d | 1.15 dd (12.8, 2.0) | 54.8 d | 1.16 dd (12.8, 2.4) |
| 6 | 24.4 t | 1.77 m 1.79 m | 28.2 t | 1.70 m 1.72 m | 28.5 t | 1.71 m 1.73 m |
| 7 | 38.5 t | 1.98 m 2.37 m | 36.5 t | 2.00 td (12.8, 4.8) 2.40 br d (12.8) | 36.8 t | 2.00 td (13.2, 4.4) 2.41 br d (12.4) |
| 8 | 147.4 s | | 148.1 s | | 148.0 s | |
| 9 | 56.3 d | 2.34 m | 60.4 d | 2.26 d (9.6) | 60.5 d | 2.26 d (10.0) |
| 10 | 38.9 s | | 38.1 s | | 38.5 s | |
| 11 | 21.4 t | 1.42 m 1.50 m | 131.5 d | 5.64 dd (15.6, 9.6) | 131.9 d | 5.67 ddd (15.2, 10.0, 1.2) |
| 12 | 28.9 t | 1.24 m 1.46 m | 127.1 d | 5.50 dd (15.6, 5.6) | 127.0 d | 5.44 dd (15.2, 6.8) |
| 13 | 39.5 d | 2.46 m | 42.2 d | 3.24 m | 42.9 d | 3.25 m |
| 14 | 29.6 t | 1.75 m 1.96 m | 29.1 t | 2.45 m 2.15 m | 29.7 t | 2.46 m 2.14 m |
| 15 | 66.4 t | 4.16 td (8.8, 6.8) 4.30 td (8.8, 2.8) | 66.5 t | 4.34 td (8.4, 3.6) 4.23 td (8.4, 6.8) | 66.6 t | 4.35 td (9.2, 4.0) 4.23 td (9.2, 6.8) |
| 16 | 179.1 s | | 177.1 s | | 176.6 s | |
| 17 | 106.7 t | 4.50 br s 4.80 br s | 108.8 t | 4.74 d (1.6) 4.50 d (1.6) | 108.2 t | 4.74 d (1.6) 4.45 d (1.6) |
| 18 | 27.1 q | 0.95 s | 22.7 q | 1.22 s | 23.0 q | 1.23 s |
| 19 | 64.9 t | 3.36 d (11.2) 3.72 d (11.2) | 64.1 t | 4.17 d (11.2) 3.30 d (11.2) | 64.2 t | 4.18 d (11.2) 3.31 d (11.2) |
| 20 | 15.3 q | 0.62 s | 15.9 q | 0.72 s | 16.2 q | 0.72 s |

$^a$Multiplicities were obtained from DEPT experiments.

proton [δ$_H$ 3.45 (dd, J=11.2, 4.4 Hz)], and two germinal carbinol protons [δ$_H$ 3.30 and 4.17 (1H each, d, J=11.2 Hz)]. The signals of the other methylene protons in the $^1$H NMR spectrum were similar to those of 5 (Reddy, M. K. et al., *Phytochemistry* 2003, 62, 1271-1275). Compound 5 has one more double bond and, therefore, one more olefinic signal than 2 in the $^1$H NMR spectrum. The $^1$H chemical shifts of H-11 and H-12 in 2 shift to higher field comparing to those of compound 5, and meanwhile compound 2 has no significant absorption in its UV spectrum. In the HMBC spectrum, the signal of H-3 (δ$_H$ 3.45) was correlated with C-18 and C-19, indicated that the hydroxyl group is linked at C-3. The H-3 proton was assigned as axially oriented according to its observed coupling constants (J=11.2, 4.4 Hz). In the NOESY spectrum, the proton signal of H-20 showed correlations with H-11 and H-19, suggesting that H-11, H-19 and H-20 were all β-oriented. The C-13 stereochemistry is uncertain. Based on the above evidence, compound 2 was proposed as 3β,19-dihydroxylabda-8(17), 11E-dien-16,15-olide.

Compound 3 was also isolated as an amorphous powder and assigned a molecular formula of C$_{20}$H$_{30}$O$_4$ from HRE-IMS and $^{13}$C NMR data. The IR absorption bands at 3391 and

Example 2

The Effects of Isolated Pure Compounds on Protection Neurons from Damage

In this study, primary cultures of neonatal cortical neurons from the cerebral cortex of Harlan Sprague-Dawley rat pups at postnatal day were used as target cells. Primary cultures of neonatal cortical neurons were prepared from the cerebral cortex of Harlan Sprague-Dawley rat pups at postnatal day 1. Briefly, each pup was decapitated and the cortex was digested in 0.5 mg/mL papain at 37° C. for 15 min. The tissue was dissociated in Hibernate A medium (containing B27 supplement) by aspirating trituration to separate cells. Cells were plated (at the density of 5×10$^4$ cells/cm$^2$) onto poly-D-lysine-coated dishes and maintained in Neurobasal medium containing B27 supplement, 10 units/mL penicillin, 10 mg/mL streptomycin, and 0.5 mg/mL glutamine (5% CO$_2$/9% O$_2$) for 3 days. Cells were then exposed to cytosine-β-D-arabinofuranoside (5 μM) for 1 day to inhibit proliferation of non-neuronal cells. The cells were used for the experiment on the fifth day.

The effects of isolated pure compounds on Aβ$_{25-35}$-treated cell apoptosis were determined by a MTT method for evaluating neuroprotective activity. The mitochondrial dehydrogenase activity was assayed by reduction cleavage of the tetrazolium salt MTT (3-[4,5-dimethylthiazol-2-yl]-2,5-diphenyltetrazolium bromide), to yield a purple dye with absorbance read at about 570 nm. Results are expressed as percentage of control absorbance. Cortical neurons prepared as described above were incubated with vehicle (0.1% DMSO) or various concentrations of the compounds for 2 h then exposed to 5 μM Aβ for 40 h. The cell viability was assessed by MTT reduction analysis. Cells were incubated with minimum essential medium containing 0.5 mg/mL MTT for 1 h. The medium was aspirated, and the formazan particle was dissolved with DMSO. The absorbance at 600 nm was measured using an enzyme-linked immunosorbent assay reader. Results are expressed as means±S.D. and were analyzed by ANOVA with post hoc multiple comparison with a Bonferroni test.

As the results showed in Table 2, the compounds 1-5 reduced Aβ-induced neurotoxicity in a concentration-dependent manner. The compounds significantly protected neurons from Aβ damage by 25.3% (compound 1), 29.5% (compound 2), 36.7% (compound 3), 28.9% (compound 4), and 29.5% (compound 5), at concentrations of 5, 10, 10, 10, and 20 μM, respectively.

TABLE 2

Protection of Cortical Neurons against Aβ-Induced Cell Death by Selected Compounds from the Fruiting Body of *Antrodia camphorata*[a]

| 5 μM Aβ plus reagent | concentration (μM) | cell death (%) |
|---|---|---|
| 1 | 1 | 34.4 ± 3.4 |
|  | 5 | 25.3 ± 5.7*** |
|  | 10 | 28.1 ± 5.7*** |
|  | 20 | 30.8 ± 5.0** |
| 2 | 1 | 43.8 ± 9.5 |
|  | 5 | 34.9 ± 2.6 |
|  | 10 | 29.5 ± 6.4* |
|  | 20 | 26.3 ± 9.4** |
| 3 | 1 | 45.1 ± 3.5 |
|  | 5 | 39.6 ± 3.4 |
|  | 10 | 36.7 ± 8.7 |
|  | 20 | 29.3 ± 10.6** |
| 4 | 1 | 41.2 ± 3.4 |
|  | 5 | 34.8 ± 3.2 |
|  | 10 | 28.9 ± 8.1** |
|  | 20 | 32.6 ± 7.2* |
| 5 | 1 | 40.7 ± 3.3 |
|  | 5 | 35.7 ± 1.9 |
|  | 10 | 30.8 ± 5.7*** |
|  | 20 | 29.5 ± 5.0*** |
| Ac-DEVD-CHO | 1 | 35.8 ± 3.5 |
|  | 5 | 30.2 ± 5.5*** |
|  | 10 | 24.5 ± 4.6*** |
|  | 20 | 23.1 ± 1.6*** |
| Vehicle (0.1% DMSO) |  | 40.5 ± 1.4 |

[a]Cortical neurons were incubated with vehicle (0.1% DMSO), Ac-DEVD-CHO (caspase 3 inhibitor for the positive control) or compounds from *Antrodia camphorata* at the indicated concentration for 2 h, then exposed to 5 μM Aβ$_{25-35}$ for 40 h. The cell viability was assessed by MTT reduction analysis. The data are means ± S.D of three independent experiments. Significant differences of cell death between cells treated with Aβ and Aβ plus compound are indicated by
*p < 0.05;
**p < 0.01; and
***p < 0.001.

What is claimed is:

1. A compound represented by the following structural formula (2):

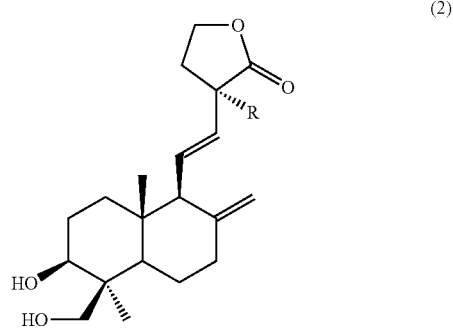

wherein R is H (α, epi-α).

2. A compound represented by the following structural formula (3):

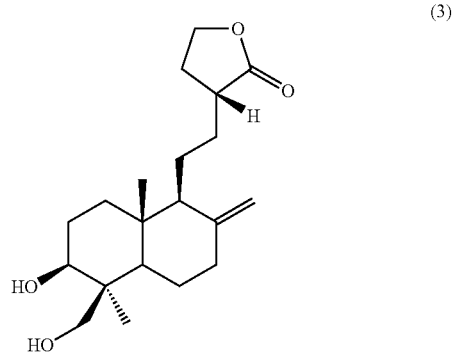

wherein R is H (β, epi-β).

3. The compound of claim 1, wherein the compound is isolated from the fruiting body of *Antrodia camphorata*.

4. The compound of claim 1, wherein the compound is 3β, 19-dihydroxylabda-8(17), 11E-dien-16, 15-olide.

5. The compound of claim 2, wherein the compound is 13-epi-3β, 19-dihydroxylabda-8(17), 11E-dien-16, 15-olide.

6. The compound of claim 2, wherein the compound is 3β, 19-dihydroxylabda-8(17), 11E-dien-16, 15-olide.

* * * * *